United States Patent [19]
Wu et al.

[11] 3,976,776
[45] Aug. 24, 1976

[54] TRANQUILIZER PROCESS EMPLOYING N-(HETEROARCYCLIC)PIPERAZINYLALK-YLAZASPIROALKANEDIONES

[75] Inventors: Yao Hua Wu; James W. Rayburn, both of Evansville, Ind.

[73] Assignee: Mead Johnson & Company, Evansville, Ind.

[22] Filed: July 14, 1975

[21] Appl. No.: 595,467

Related U.S. Application Data

[62] Division of Ser. No. 312,543, Dec. 6, 1972, Pat. No. 3,907,801, which is a division of Ser. No. 879,604, Nov. 24, 1969, Pat. No. 3,717,634.

[52] U.S. Cl. ................................ 424/251; 424/249; 424/250; 424/263; 424/273
[51] Int. Cl.² ................ A61K 31/44; A61K 31/495; A61K 31/505; A61K 31/50
[58] Field of Search ............ 424/251, 250, 269, 249

[56] References Cited
UNITED STATES PATENTS
3,398,151   8/1968   Wu .............................. 260/268 PH

*Primary Examiner*—Stanley J. Friedman
*Attorney, Agent, or Firm*—R. E. Carnahan; R. H. Uloth

[57] ABSTRACT

The present invention concerns the class of heterocyclic carbon compounds comprised of N-(heteroarcyclic)piperazinylalkyl derivatives of azaspiroalkanediones which have potent and specific tranquilizing action and anti-emetic properties. Typical embodiments of this invention are 8-[4-[4-(2-pyrimidinyl)-1-piperazinyl]butyl]-8-azaspiro[4.5]decane-7,9-dione and 8-[4-[4-(2-pyridyl)-1-piperazinyl]-butyl]-8-azaspiro[4.5]decane-7,9-dione.

38 Claims, No Drawings

TRANQUILIZER PROCESS EMPLOYING N-(HETEROARCYCLIC)PIPERAZINYLALK-YLAZASPIROALKANEDIONES

CROSS-REFERENCE TO RELATED APPLICATION

This application is a divisional application of our copending application Ser. No. 312,543 filed Dec. 6, 1972, now U.S. Pat. No. 3,907,801 which is a divisional application of Ser. No. 879,604 filed Nov. 24, 1969, and now U.S. Pat. No.3,717,634 patented Feb. 20, 1973.

SUMMARY OF THE INVENTION

This invention relates to new compounds characterized by the following general structural formula and the non-toxic pharmaceutically acceptable acid addition salts thereof.

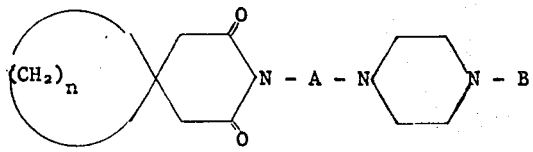

In the foregoing Formula I, $m$ is the integer 4 or 5. The symbol —A— which connects the sprioglutarimide and the N-(heteroarcyclic)piperazine represents a divalent alkylene chain of 2 to 6 carbon atoms inclusive. Said alkylene chain can be straight- or branched-chain hydrocarbon grouping in which the ring connecting bonds are on different carbon atoms such as- 1,2-ethylene(—CH$_2$CH$_2$—)

trimethylene(—CH$_2$CH$_2$CH$_2$—)

1,2-propylene(—CH$_2$CH—)
$\qquad\qquad\qquad$ |
$\qquad\qquad\qquad$ CH$_3$ tetramethylene(—CH$_2$CH$_2$CH$_2$CH$_2$—)

$\qquad\qquad\qquad\quad$ CH$_3$
$\qquad\qquad\qquad\quad$ |
2-methyl-1,2-propylene(—CH$_2$C$\quad$ )
$\qquad\qquad\qquad\quad$ |
$\qquad\qquad\qquad\quad$ CH$_3$ hexamethylene(—CH$_2$CH$_2$CH$_2$CH$_2$CH$_2$CH$_2$—)

and the like. The piperazine substituent represented by the symbol "B" is selected from the group consisting of 2-imidazolyl and a heteroarcyclic. Said heteroarcyclic is represented by the symbol:

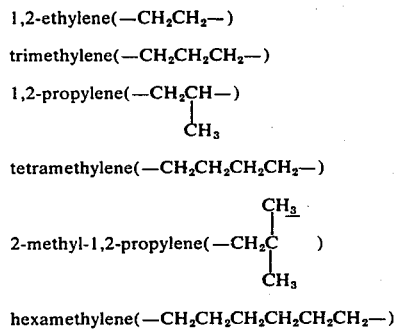

wherein W and Y are independently selected from the group consisting of CH and nitrogen. By the term "heteroarcyclic" as used herein, it is meant substituents comprised of nitrogen, carbon, and hydrogen which when taken together form a heteroaromatic system. The $R^1$ and $R^2$ substituents of the heteroarcyclic referred to above are independently selected from the group consisting of hydrogen, lower alkyl from 1 to 4 carbon atoms inclusive, alkoxy of from 1 to 4 carbon atoms inclusive, hydroxy, amino, alkylthio of 1 to 4 carbon atoms inclusive, halogen, trifluoromethyl, alkanoamido of from 1 to 6 carbon atoms inclusive, and alkanesulfonamido of 1 to 6 carbon atoms inclusive. By the term "lower alkyl" as employed herein it is meant straight or branched chain alkyl radicals including methyl, ethyl, propyl, isopropyl, 1-butyl, 1-methylpropyl, 2-methylpropyl, and tert.-butyl. Similarly, the alkyl fragment of the alkylthio substituent refers to straight or branched chain radicals described above. Straight or the branched chain alkanes of 1 to 6 carbon atoms inclusive comprise the alkane radical of alkanoamido and alkanesulfonamido groupings.

The term "non-toxic pharmaceutically acceptable acid addition salts" as used herein refers to a combination of compounds of the present invention with relatively nontoxic inorganic or organic acids. Illustrative of the variety of acids which may be used are sulfuric, phosphoric, hydrochloric, hydrobromic, hydroiodic, sulfamic, methanesulfonic, benzenesulfonic, para-toluenesulfonic, acetic lactic, succinic, maleic, tartaric, citric, gluconic, ascorbic, benzoic, cinnamic, and related acids.

Conversion of the compounds of the present invention to pharmaceutically acceptable acid addition salts is accomplished by admixture of these compounds with substantially one chemical equivalent of any of the various acids hereinbefore defined. Generally the reactions are carried out in an inert solvent. Suitable solvents, merely by way of example, are ethanol, benzene, ethyl acetate, ether, and halogenated hydrocarbons.

Illustrative of the nomenclature employed herein for the naming of the products of this invention are partial structures corresponding to the substituted glutarimide portions of Formula I are shown below with the positions numbered.

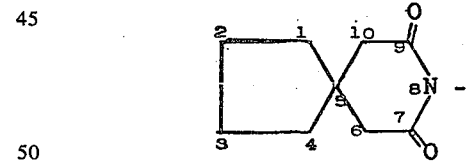

8-Azaspiro[4.5]decane-7,9-dione Formula I, $n$=4

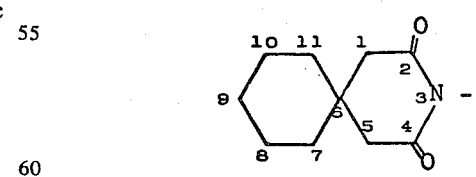

3-Azaspiro[5.5]undecane-2,4dione Formula I, $n$=5

Compounds of Formula I which are particularly preferred embodiments of the present invention are those wherein "$n$" is the integer 4, the divalent alkylene chain "—A—" is a chain of 4 carbon atoms inclusive and the heteroarcyclic "B" substituent is a 2-pyridyl or a 2-pyrimidyl group having $R^1$ and $R^2$ substituents with the meanings hereinbefore stated. Representative of these compounds are the individually preferred compounds 8-[4-[4-(2-pyrimidinyl)-1-piperazinyl]butyl]-8-azaspiro[4.5]decane-7,9-dione and 8-[4-[4-(2-pyridyl)-1-piperazinyl]butyl]-8-azaspiro[4.5]-decane-7,9-dione.

General embodiments of the process for the preparation of compounds of the present invention are schematically illustrated below and labeled Method A, Method B and Method C. The use of a particular method to produce compounds embraced by this invention is dictated to a large extent by conditions which will be apparent to those skilled in the art. In practice, the selection of the method used for the preparation of any one compound of the present invention is principally determined by the commercial availability of the necessary intermediates and/or by the ease which available compounds can be converted to desired intermediates.

chloride, bromide, iodide, sulfate, phosphate, tosylate or mesylate. M comprises an alkali metal salt of the substituted glutarimide and is preferably sodium or potassium.

Method A is carried out by reacting a spirosubstituted glutaric anhydride of Formula II with the 1-(ω-aminoalkyl)-4-(heteroarcyclic)piperazines of Formula III to provide products of Formula I. Preferably, the reaction is carried out at elevated temperatures in a reaction inert organic solvent. By the term "inert organic solvent", as referred to herein is meant any protic or aprotic solvent or diluent which does not enter into the reaction to any substantial degree. Pyridine is the preferred solvent. Temperatures of about 100°C. to about 200°C. are preferred to facilitate completion of the reaction. The duration of the reaction is critical only to the extent of providing maximum yields and reaction periods of from about 16 hr. to as much as 11 days are preferred. The lengthy reaction periods are

METHOD A

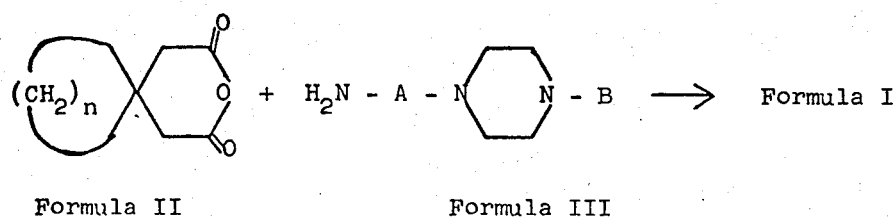

Formula II        Formula III

METHOD B

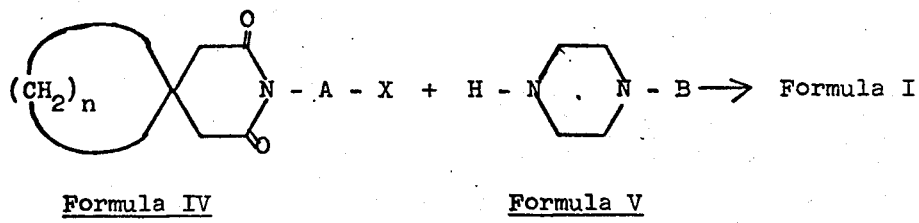

Formula IV        Formula V

METHOD C

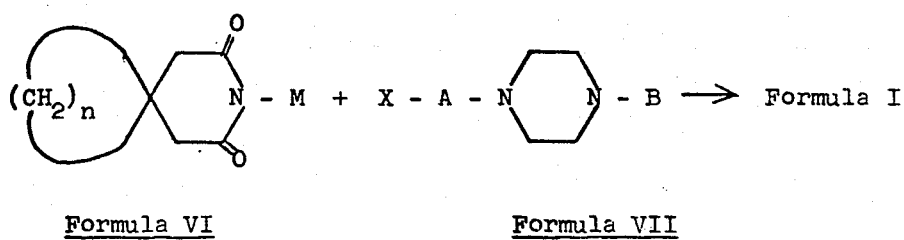

Formula VI        Formula VII

In the foregoing reaction schemes, the symbols $n$, —A—, and B have the same meanings as previously defined relative to Formula I. The symbol X refers to the acid residue of a reactive ester grouping such as a necessary in some instances to obtain complete conversion of glutaric acid half-amides of Formula VIII which are initially formed when an anhydride of Formula II is combined with an amine of Formula III.

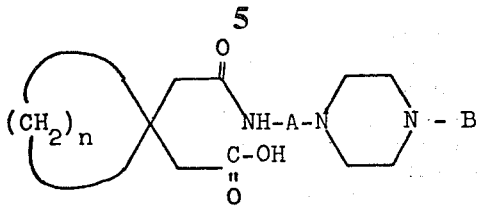

Formula VIII

The glutaric acid half-amides of Formula VIII may be also transformed into Formula I products by heating in boiling acetic anhydride which is a well known standard organic procedure for ring closure useful in the formation of cyclic imides.

Method B is carried out under reaction conditions amply described in literature wherein tertiary amines are formed by alkylation of a secondary amine with an alkyl halide, sulfate, phosphate, tosylate, or mesylate. The Formula IV and Formula V intermediates are preferably reacted in an inert liquid reaction medium at temperatures of from about 60°C. to about 200°C. in the presence of a base suitable for use as an acid binding agent. Sodium carbonate is a particularly preferred acid binding agent but other inorganic and tertiary organic base may be employed including other alkali and alkaline earth metal carbonates, bicarbonates, or hydrides and tertiary amines. Reaction periods ranging from about 2 hrs. to approximately 4 days are preferred in order to obtain satisfactory yields of the present compounds. A particularly preferred solvent is n-butanol but any inert reaction medium is generally applicable to use in this reaction. To a large extent, the duration of the reaction period depends upon the temperature and reaction solvent selected. By way of illustration, alkylation is facilitated and the reaction period is appreciably shortened if dimethylformamide is employed as the reaction medium compared to a solvent such as benzene.

Method C is another method useful for preparation of compounds of Formula I. In this method, the spiroglutarimide metal salt depicted by Formula VI is reacted with substituted piperazines of Formula VII. Standard laboratory procedures are employed in carrying out the reaction such as those described for the alkylation step of the Gabriel synthesis—S. Gabriel, Ber. 20, 2224 (1887). For example, the reactants are combined in an inert reaction medium at temperatures ranging from about 25°C. to 200°C. Preferred solvents for carrying out the reaction are dimethylformamide, acetone, benzene, n-butanol, ethanol and the like.

With respect to the reactants for Methods A, B and C, many of them, including 3,3-tetramethyleneglutaric anhydride, (Formula II, $n=4$) are known compounds which are readily available from commercial sources. Others, which are not commercially available, can be prepared in accordance with standard synthetic procedures which are known to those skilled in the art.

Preparation of N-(heteroarcyclic)piperazines of Formula V have been described by K. L. Howard et al. in J. Org. Chem., 18, 1484 (1953). Their procedures are applicable to the preparation of other N-(heteroarcyclic)piperazine intermediates not specifically disclosed but which are required for the preparation of compounds embraced in the present invention.

The 1-(ω-aminoalkyl)-4-(heteroarcyclic)piperazine of Formula III are obtained according to methods described in U.S. Pat. No. 3,398,151 by alkylation of N-(heteroarcyclic)piperazines of Formula V with haloalkylnitriles to provide 1-(ω-cyanoalkyl)-4-(heteroarcyclic)piperazine intermediates which are subsequently reduced to the Formula III substituted piperazines. Reduction of the cyano intermediate may be carried out catalytically, preferably with W-6 Raney Nickel catalyst under high pressure, or alternatively with hydrazine and W-6 Raney Nickel.

The intermediate azaspirodecane- and undecanediones of Formula IV having the —A—X group attached to the nitrogen atom are prepared according to procedures described in U.S. Pat. No. 3,398,151. Reaction of the glutaric anhydrides of Formula II with an alkanolamine of the formula $H_2N$—A—OH are carried out under conditions similar to those described hereinabove for Method A. The resulting intermediate glutarimide has the structure shown for Formula IV wherein X is OH. Esterification of this material is accomplished by conventional techniques well known to the art to provide the intermediate of Formula IV. Preferably, thionyl chloride is reacted with the alcohol precursor of Formula IV (X=OH) to provide the intermediate wherein X is chlorine. Conventional techniques which are adequately described in the literature are employed to provide the bromides, iodides, phosphates, sulfates, tosylates, and mesylates corresponding to Formula IV.

The piperazine reactant of Formula VII having the X—A— grouping attached to the nitrogen atom is prepared according to standard organic procedures. By way of example, reaction of the piperazines of Formula V with alkanol halides of the Formula HO—A—X provides intermediate of Formula VIII.

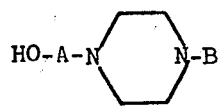

Formula VIII

This intermediate is then esterified according to conventional techniques well known to the art to provide the Formula VII reactants. For instance, thionyl chloride acting upon the compounds of Formula VIII provides the Formula VII intermediate in which X is chlorine. In a similar fashion, bromides, and iodides are prepared. Phosphates, sulfates, tosylates, mesylates corresponding to Formula VII are obtained with conventional laboratory techniques.

General embodiments of the process of the present invention for the preparation of compounds of Formula I as hereinabove described are considered to be a unitary process. Thus, the azaspiroalkanedione of Formula I are prepared in accordance with the unitary process of the present invention by reacting a piperazine of the Formula IX.

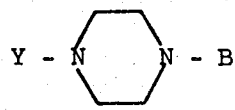

Formula IX wherein Y is selected from the group consisting of hydrogen (Formula IXa), $H_2N$—A— (Formula IXb), or X—A— (Formula IXc), and A and X are as hereinbefore defined, with a spiroglutaric acid anhydride of Formula II.

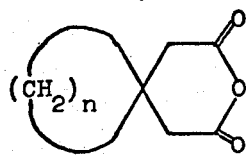

Formula II wherein *n* is as hereinbefore defined, when Y is the group H₂N—A—; or a N-substituted spiro-glutaric acid imide of Formula IV.

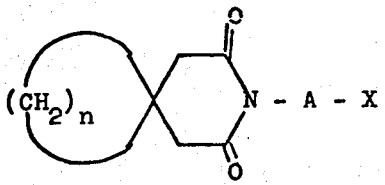

Formula IV wherein A and *n* are as hereinbefore defined and X is a reactive ester group, when Y is hydrogen; or a spiro-glutarimide of Formula VI.

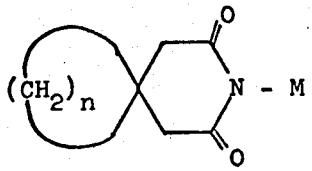

Formula VI wherein *n* and M are as hereinbefore defined, when Y is the group X—A—; in the presence of a reaction inert solvent at an elevated temperature.

The present invention relates to azaspirodecanedione and azaspiroundecanedione derivatives as hereinabove described by Formula I. In U.S. Pat. No. 3,398,151 reference is also made to derivatives of azaspirodecanediones and azaspiroundecanediones which have a number of pharmacological activities including tranquilizing action. In the instant case, it has been discovered that N-(heteroarcyclic)piperazine alkyl derivatives of azaspirodecanediones and azaspiroundecanediones are highly active and specific tranquilizing agents and in addition also exhibit anti-emetic properties. Present compounds are improved tranquilizing agents compared to the azaspirodecanediones and azaspiroundecanediones of U.S. Pat. No. 3,398,151, in that tranquilizing activity is more potent and specific.

With respect to side effects such as sedative and alpha-adrenergic blockade which are exhibited by a number of prominent tranquilizing agents the present compounds are unique in that such adverse reaction is substantially diminished or practically non-existent. By way of illustration, 8-[4-[4-(2-pyrimidinyl)-1-piperazinyl]butyl]-8-azaspiro-[4.5]decane-7,9-dione hydrochloride has only about 1/400 th. the alpha-adrenergic blocking activity of the well known tranquilizer, chlorpromazine.

Tranquilizing properties of the compounds of this invention can be demonstrated in rats by a shuttle box technique described by J. R. Albert and L. E. Allen in the Pharmacologist 4,152 (1962). This test is designed to differentiate tranquilizing agents from non-specific central nervous system depressants such as sedatives and hypnotics. Tranquilizing effects are observed when the compounds of the present invention are administered intraperitoneally to the rat in dosages ranging from 1.5 to 180 mg./kg. of body weight.

The tranquilizing action of the compounds of the present invention can be demonstrated in Rhesus monkeys by observing general behavioral effects. Intramuscular administration of present compounds to the monkey in dosages ranging from 2 to 16 mg./kg. of body weight affords tranquilizing effects similar to those produced by chlorpromazine.

The compounds of the present invention are relatively non-toxic compounds. For example, the intraperitoneal 50% lethality dose of 8-[4-[4-(2-pyrimidinyl)-1-piperazinyl]butyl]-8-azaspiro[4.5]decane-7,9-dione hydrochloride is 146 mg./kg. of body weight in the mouse.

Systemic administration of the compounds of the present invention to mammals in dosages ranging from about 0.01 to 40 mg./kg. of body weight per day induce effective tranquilizing responses in the mammalian recipient. Oral, parenteral and rectal routes are preferred forms of systemic administration. Forms of parenteral administration include intramuscular, intravenous, and subcutaneous administration. Those skilled in the art will recognize that the dosage of the compounds of the present invention will vary with the form and mode of administration and in some instances with the particular compound chosen. Generally, it will be found that when a compound of the present invention is administered orally, a larger quantity of the active agent is required to produce the same effect as a smaller quantity thereof which is given parenterally. It is generally preferred to administer the compounds of this invention at a concentration level that will produce effective tranquilizing effects without causing any harmful or deleterious side effects.

For pharmaceutical purposes, the compounds of Formula I may be administered to mammals in the form of free bases or in the form of non-toxic acid additon salts. In the free base form, the compounds are relatively insoluble in water but are soluble in most organic solvents such as lower alkyl alcohols, esters, acetones, chloroform and the like. The present compounds in the form their acid addition salts are, in general, soluble in water and methanol but relatively insoluble in solvents such as benzene, ether, petroleum ether and the like. In either the free base or the acid addition salt form, the compounds of Formula I may be compounded and formulated into pharmaceutical compositions and unit dosage suitable for systemic administration. Organic or inorganic solid materials or liquids which are pharmaceutically acceptable carriers are employed in these pharmaceutical compositions. By the term "systemic administration" as used herein it is meant forms of administration such as oral, parenteral and rectal. Pharmaceutical compositions considered within the scope of this invention may take the form of tablets, powder, granules, capsules, suspensions, solutions, suppositorys, elixirs, ointments and the like. Unit dosages ranging from about 1 to 500 mg. are employed. Suitable pharmaceutical carriers comprise both solids and liquids such as corn starch, lactose, calcium phosphate, stearic acid, polyethylene glycol, water, sesame seed oil, peanut oil, propylene glycol, and the like.

DESCRIPTION OF THE PREFERRED EMBODIMENTS

The following examples are illustrative of the process and products of the present invention and are not to be construed as limitations of this invention, many variations of which are possible without departing from the spirit and scope thereof.

METHOD A

Procedure 1. Condensation with Substituted Glutaric Anhydride.

A mixture of 0.1 mole of the substituted glutaric anhydride (Formula II), 0.1 mole of 1-ω-aminoalkyl)-4-(heterocycle)piperazine (Formula III), and 300 ml. of pyridine is refluxed until imide formation is complete. The degree of reaction is readily followed by taking an aliquot portion of the reaction mixture, removing the solvent, and obtaining the infrared absorption spectrum of the residue. When reaction is complete, the spectrum exhibits typical infrared imide bands at 1700 and 1710 cm.$^{-1}$ whereas if incomplete, the infrared spectrum contains amide and carboxyl absorption bands at 1680, 1760, and 3300 cm.$^{-1}$ The azaspiroalkanedione product is purified as the free base by stripping off the pyridine solvent and crystallizing the residue from a suitable solvent or by vacuum distillation thereof.

Suitable acid addition salts of the product are prepared by treating an ethanol solution of the free base with an equi-molar amount of the appropriate acid.

Examples of representative compounds of the present invention prepared according to Procedure 1 are indicated in Table I.

TABLE I

8-[4-(N-HETEROARCYCLIC)-1-PIPERAZINYLALKYL]-8-AZASPIRO[4.5]DECANE-7,9-DIONE PRODUCTS

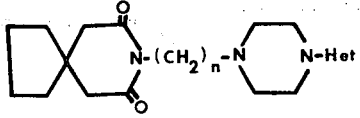

| Example No. | Method | PRODUCT n | Het. | BASE B.P.,°C (mm Hg) | Percent Yield | M.P.°C. | HYDOCHLORIDE Crystn. Solvent | Formula | Analyses | |
|---|---|---|---|---|---|---|---|---|---|---|
| 1 | A | 2 | (pyridine) | — | — | 208.5–209.5 | ethanol | $C_{20}H_{28}N_4O_2 \cdot HCl$ | C | 61.11 |
| | | | | | | | | | H | 7.25 |
| | | | | | | | | | N | 14.26 |
| | | | | | | | | | Cl | 8.81 |
| 2 | A | 4 | (pyridine) | 255–260 (0.1) | 76 | 172–173.5 | 2-butanone | $C_{22}H_{32}N_4O_2 \cdot HCl$ | C | 63.01 |
| | | | | | | | | | H | 7.89 |
| | | | | | | | | | N | 13.55 |
| | | | | | | | | | Cl | 8.29 |
| 3 | A | 2 | (pyrimidine) | 230–250 (0.1) | 90 | 206–207 | absolute ethanol | $C_{19}H_{27}N_5O_2 \cdot HCl$ | C | 58.00 |
| | | | | | | | | | H | 7.23 |
| | | | | | | | | | N | 17.75 |
| | | | | | | | | | Cl | 9.03 |
| 4 | B | 3 | (pyrimidine) | — | — | 214–215 | absolute ethanol-ether | $C_{20}H_{29}N_5O_2 \cdot HCl$ | C | 59.06 |
| | | | | | | | | | H | 7.30 |
| | | | | | | | | | N | 17.24 |
| 5 | A | 4 | (pyrimidine) | 240–265 (0.1) | 67 | 201.5–202.5 | absolute ethanol | $C_{21}H_{31}N_5O_2 \cdot HCl$ | C | 60.29 |
| | | | | | | | | | H | 7.41 |
| | | | | | | | | | N | 16.60 |
| | | | | | | | | | Cl | 8.48 |
| 6 | A | 5 | (pyrimidine) | 260–275 (0.07) | 52 | 188.5–190.5 | methanol-ethyl acetate | $C_{22}H_{33}N_5O_2 \cdot HCl$ | C | 60.44 |
| | | | | | | | | | H | 7.93 |
| | | | | | | | | | N | 16.01 |
| 7 | B | 3 | (methoxy-pyrimidine) | 260–270 (0.2) | 59 | 233.5–234.5 | ethanol | $C_{22}H_{32}N_4O_3 \cdot HCl$ | C | 60.72 |
| | | | | | | | | | H | 7.73 |
| | | | | | | | | | N | 13.01 |
| | | | | | | | | | Cl | 7.98 |

METHOD B

Procedure 2. Alkylation of N-(heteroarcyclic)piperazines.

A mixture of 4.9 g. (0.02 mole) of 8-[3-chloro-1-propyl]-8-azaspiro[4.5]decane-7,9-dione, 3.3 g. (0.02 mole) prepared in the manner of U.S. Pat. No. 3,398,151, N-(2-pyrimidyl)piperazine, and 2.2 g. (0.02 mole) of sodium carbonate in 75 ml. of n-butanol is refluxed for three days and filtered. The filtrate is concentrated in vacuo and the residue taken up in 100 ml. of benzene. Addition of 4.0 ml. of 5.0 N ethanolic hydrogen chloride to the benzene solution of the free base provides the product 8-[3-[4-(2-pyrimidinyl)-1-piperazinyl]propyl]-8-azaspiro[4.5]decane-7,9-dione as a hydrochloride salt which is collected and crystalized from absolute ethanol-ether, yield 3.4 g., m.p. 214°–215°C. (corr.).

Examples of representative products of this invention and physical properties thereof prepared according to Method B are listed in Table I.

METHOD C

Procedure 3. Alkylation of Azaspiroalkaneimides.

A solution of 0.1 mole of 3,3-tetramethyleneglutarimide in methanol (150 ml.) is treated with 0.1 mole of sodium methoxide. The solvent is removed in vacuo to provide a residue consisting of the sodium salt of 3,3-tetramethyleneglutarimide which without further purification is combined with 0.1 mole of 1-(2-chlorobutyl)-4-(pyrimidinyl)piperazine in 150 ml. of n-butanol. The mixture is refluxed for a period of time of sufficient duration to provide approximately 0.1 mole of precipitated sodium chloride as a by-product. Isolation of the product by standard laboratory procedures provide 8-[3-[4-(2-pyrimidinyl)-1-piperazinyl]propyl]-8-azaspiro[4.5]decane-7,9-dione which is also a product of Procedure 2.

Examples 8-28

Additional exemplification of compounds of the present invention is given in Table II along with the mode of preparation according to Method A, Method B, or Method C and the appropriate intermediates. Although only a single method of preparation is indicated for each example, one skilled in the art can readily appreciate that any of the Methods A, B and C hereinabove described are equally applicable to the preparation of the compounds of the present invention.

TABLE II

Additional N-(HETEROARCYCLIC)PIPERAZINYLALKYLAZASPIROALKANEDIONES

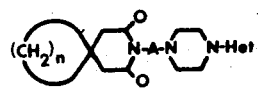

| Example No. | n | A | Product Het. | Method | Intermediates |
|---|---|---|---|---|---|
| 8 | 5 | —(CH₂)₄— | (pyrimidinyl) | A | 3,3-pentamethyleneglutaric anhydride and 1-(4-aminobutyl)-4-[2-(pyrimidinyl)]piperazine |
| 9 | 5 | —(CH₂)₄— | (2,6-diaminopyrimidinyl) | A | 3,3-pentamethyleneglutaric anhydride and 1-(4-aminobutyl)-4-[4-(2,6-diaminopyrimidinyl)]piperazine |
| 10 | 4 | —(CH₂)₄— | (2-amino-6-methylpyrimidinyl) | A | 3,3-tetramethyleneglutaric anhydride and 1-(4-aminobutyl)-4-[4-(2-amino-6-methylpyrimidinyl)]piperazine |
| 11 | 4 | —(CH₂)₄— | (4,6-dimethoxypyrimidinyl) | A | 3,3-tetramethyleneglutaric anhydride and 1-(4-aminobutyl)-4-[2-(4,6-dimethoxypyrimidinyl)]piperazine |
| 12* | 4 | —(CH₂)₄— | (4,6-dimethylpyrimidinyl) | A | 3,3-tetramethyleneglutaric anhydride and 2-(4-aminobutyl)-4-[2-(4,6-dimethylpyrimidinyl)]piperazine |

TABLE II-continued

Additional N-(HETEROARCYCLIC)PIPERAZINYLALKYLAZASPIROALKANEDIONES

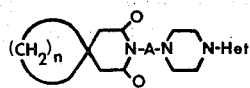

| Example No. | n | A | Product Het. | Method | Intermediates |
|---|---|---|---|---|---|
| 13 | 4 | —(CH₂)₄— | 2-SCH₃-pyrimidinyl | A | 3,3-tetramethyleneglutaric anhydride and 1-(4-aminobutyl)-4-[4-(2-methylthio)pyrimidinyl)]piperazine |
| 14 | 4 | —(CH₂)₄— | 4,6-dichloropyrimidin-2-yl | A | 3,3-tetramethyleneglutaric anhydride and 1-(4-aminobutyl)-4-[2-(4,6-dichloropyrimidinyl)]piperazine |
| 15 | 4 | —(CH₂)₄— | 2-chloropyrimidin-4-yl | A | 3,3-tetramethyleneglutaric anhydride and 1-(4-aminobutyl)-4-[4-(2-chloropyrimidinyl)]piperazine |
| 16 | 4 | —(CH₂)₄— | 2-NO₂-6-CH₃-pyrimidin-4-yl | B | 8-(4-chlorobutyl)-8-azaspiro[4.5]decane-7,9-dione and 1-[4-(2-nitro-6-methylpyrimidinyl)]piperazine |
| 17 | 4 | —(CH₂)₄— | 2-NHSO₂CH₃-6-CH₃-pyrimidin-4-yl | A | 3,3-tetramethyleneglutaric anhydride and 1-(4-aminobutyl)-4-[4-(2-methanesulfonamido-6-methylpyrimidinyl]piperazine |
| 18 | 5 | —(CH₂)₂— | 5-NO₂-pyrimidin-2-yl | C | 3,3-pentamethyleneglutarimide and 1-(2-chloroethyl)-4-[2-(5-nitropyrimidinyl)]piperazine |
| 19 | 5 | —(CH₂)₆— | 5-NHSO₂-nC₄H₉-pyrimidin-2-yl | A | 3,3-pentamethyleneglutaric anhydride and 1-(6-chlorohexyl)-4-[2-(5-n-butanesulfonamidopyrimidinyl)]piperazine |
| 20 | 4 | —(CH₂)₄— | 4-C(CH₃)₃-pyrimidin-2-yl | C | 3,3-tetramethyleneglutarimide and 1-(4-chloroethyl)-4-[4-tert.-butylpyrimidinyl)]piperazine |
| 21 | 4 | —(CH₂)₄— | 4-O-C(CH₃)₃-pyridin-2-yl | B | 8-(4-chlorobutyl)-8-azaspiro[4.5]decane-7,9-dione and 1-[2-(4-tert.-butylpyrimidinyl)]piperazine |
| 22 | 4 | —(CH₂)₄— | 6-CF₃-pyridin-2-yl | B | 8-(4-chlorobutyl)-8-azaspiro[4.5]decane-7,9-dione and 1-[2-(6-trifluoromethylpyridinyl)]piperazine |
| 23 | 4 | —(CH₂)₄— | 1,3,5-triazin-2-yl | A | 3,3-tetramethyleneglutaric anhydride and 1-(4-aminobutyl)-4-[2-(1,3,5-triazinyl)]piperazine |
| 24 | 4 | —(CH₂)₂— | 4-NO₂-1,3,5-triazin-2-yl | C | 3,3-tetramethyleneglutarimide and 1-(2-chloroethyl)-4-[2-(4-nitro-1,3,5-triazinyl)]piperazine |
| 25 | 4 | —(CH₂)₄— | 3-NHCOC₂H₅-pyridin-2-yl | A | 3,3-tetramethyleneglutaric anhydride and 1-(4-aminobutyl)-4-[2-(3-propionylamidopyridinyl)]piperazine |
| 26 | 4 | —(CH₂)₄— | 2,6-bis(NHSO₂CH₃)-pyrimidin-4-yl | A | 3,3-tetramethyleneglutaric anhydride and 1-(4-aminobutyl)-4-[4-(2,6-dimethanesulfonamidopyrimidinyl)]piperazine |
| 27 | 4 | —(CH₂)₄— | 4-OH-pyrimidin-2-yl | A | 3,3-tetramethyleneglutaric anhydride and 1-(4-aminobutyl)-4-[2-(4-hydroxypyrimidinyl)piperazine |
| 28 | 5 | —(CH₂)₄— | 2-pyridinyl | A | 3,3-pentamethyleneglutaric anhydride and 1-(4-aminobutyl)-4-(2-pyridinyl)piperazine |

*8-[4-[4-(4,6-dimethyl-2-pyrimidinyl)-1-piperazinyl]butyl]-8-azaspiro[4.5]decane-7,9-dione hydrochloride. m.p. 216.5–217.5°C. (corr.), crystallized from absolute ethanol-anhydrous ether. Analysis - Calcd. for C₂₃H₃₆ClN₅O₂: C, 61.38; H, 8.06; N, 15.56. Found: C, 61.26; H, 8.10; N, 15.33.

Procedure 4. 1-(3-Cyanopropyl)-4-(2-pyrimidinyl)-piperazine.

A mixture of 1-(2-pyrimidinyl)piperazine (6.0 g., 0.04 mole), 4.6 g., (0.044 mole) of 3-chloropropionitrile and sodium carbonate (4.24 g., 0.04 mole) in 50 ml. of n-butanol is gently refluxed for 16 hours. The reaction mixture is concentrated in vacuo and the residual oil dissolved in about 100 ml. of cyclohexane. On standing a white crystalline material separates which is crystallized from cyclohexane to provide 6.5 g. (yield 70%) of the cyano intermediate, m.p. 56.6°–58°C. Representative examples of cyano intermediates useful in Procedure 5 along with information relative to the preparation thereof according to Procedure 4 are listed in Table III.

TABLE III

1-(ω-CYANOALKYL)-4-(HETEROARCYCLIC)PIPERAZINES

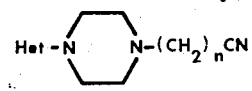

| Intermediate No. | Het. | n | Yield | B.P.,°C. (mm Hg) | M.P.°C. (Crystn. Solv.) | Formula | C | Analysis H | N |
|---|---|---|---|---|---|---|---|---|---|
| 1 | pyridyl | 1 | 82 | 163–165 (0.08) | — | $C_{11}H_{14}N_4$ | — | — | — |
| 2 | pyridyl | 3 | 92 | 185–205 (0.02) | 47–49 (cyclohexane) | $C_{13}H_{18}N_4$ | — | — | — |
| 3 | pyrimidyl | 1 | 80 | — | 98–100 (cyclohexane) | $C_{10}H_{13}N_5$ | 59.12 | 6.62 | 34.77 |
| 4 | pyrimidyl | 3 | 70 | — | 56–58 (cyclohexane) | $C_{12}H_{17}N_5$ | 62.04 | 7.31 | 30.08 |
| 5 | pyrimidyl | 4 | 80 | — | 77–78 (cyclohexane) | $C_{13}H_{19}N_5$ | 63.49 | 7.62 | 28.41 |
| 6 | 2,6-diamino-pyrimidyl | 3 | 87 | — | 191–192 (methanol) | $C_{12}H_{19}N_7$ | 55.07 | 7.28 | 37.84 |
| 7 | 2,6-dimethoxy-pyrimidyl | 3 | 46 | 220–235 (0.1) | — | $C_{14}H_{21}N_5O_2$ | 56.90 | 7.01 | 23.41 |
| 8 | 2-amino-6-methyl-pyrimidyl | 3 | 100 (Crude) | 245 (0.15) | 109–110 (ethyl acetate-Skillysolve F) | $C_{13}H_{20}N_6$ | 59.94 | 7.66 | 32.48 |

Procedure 5. 1-(4-Aminobutyl)-4-(2-pyrimidinyl)-piperazine.

A. A solution of 1.5 g. (0.05 mole) of 1-(3-cyanopropyl)-4-(2-pyrimidinyl)piperazine in 150 ml. of absolute ethanol is saturated with ammonia. W-6 Raney Nickel catalyst is added and the mixture hydrogenated under 1200 p.s.i. When the hydrogenation is completed the mixture is filtered and the residual oil distilled under reduced pressure to provide 8.2 g. (70%) of 1-(4-aminobutyl)-4-(2-pyrimidinyl)piperazine.

Reduction of cyano intermdiates of Procedure 4 in the manner described for Procedure 5 or alternatively by reduction with hydrazine and Raney Nickel provide the amino intermediates of Formula III. The following procedure is illustrative of hydrazine and Raney Nickel reductions.

B. Hydrazine hydrate 85% (640 ml) is added dropwise to 4-[-(2-pyrimidinyl)-1-piperazinyl]butyronitrile (189.8 g., 0.82 mole), Raney Nickel (190 g. - wet with water, activated by washing with 2-propanol) and 2-propanol (1.4 liter) in 2 hours at reflux. The reaction is stirred for 5 minutes, filtered, concentrated in vacuo and the residual material distilled to yield 168.2 g. (87%) of 1-(4-aminobutyl)-4-(2-pyrimidinyl)piperazine, b.p. 143°–6°C. at 0.1 mm ($N_D^{26}$ 1.5582).

Procedue 6. Solution for Parenteral Injection.

The azaspiroalkanedione compounds of the present invention are formulated for parenteral administration according to the following example. A sterile solution suitable for intraveneous injection is prepared by dissolving 21.9 g. of 8-[4-[4-(2-pyrimidinyl)-2-piperazinyl]butyl]-8-azaspiro-[4.5]decane-7,9-dione hydrochloride in 2 liters of water for injection, USP. The solution is adjusted to pH 4.2 with 0.1 N-sodium hydroxide. After adjusting the pH, the solution is sterilized by passage through a bacteriological filter and 10 ml. glass ampules aseptically filled in order to provide 10 mg. of active ingredient per ampule.

Procedure 7. Tablets.

The azaspiroalkanedione compounds of the present invention are compounded into tablets in accord with the following example.

| Material | Amount |
| --- | --- |
| 8-[4-[4-(2-pyrimidinyl)-1-piperazinyl]-butyl]-8-azaspiro[4.5]decane-7,9-dione hydrochloride | 54.8 g. |
| Magnesium Stearate | 1.3 g. |
| Corn starch | 12.4 g. |
| Corn starch pregelatinized | 1.3 g. |
| Lactose | 180.2 g. |

The foregoing materials are blended in a twin-shell blender and then granulated and pressed into tablets weighing 250 mg. each. Each tablet contains 50 mg. of active ingredient.

What is claimed:

1. The process for eliciting tranquilizing effect in a mammal which comprises administering systemically to a mammal in need thereof an effective tranquilizer dose of from about 0.01 to about 40 mg./kg. of body weight of said host of a compound selected from a group consisting of compounds having the formula:

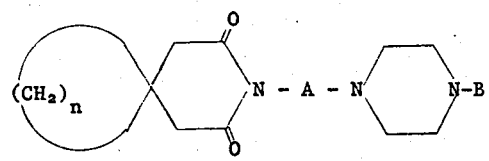

wherein $n$ is the integer 4 or 5;

A is a divalent straight or branched alkylene chain of 2 to 6 carbon atoms inclusive and connects the nitrogen atoms as shown through at least 2 carbon atoms;

B is a heteroarcyclic represented by the symbol

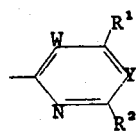

wherein

W and Y are independently selected from the group consisting of CH and nitrogen, $R^1$ and $R^2$ are independently selected from the group consisting of hydrogen, lower alkyl from 1 to 4 carbon atoms inclusive, lower alkoxy of from 1 to 4 carbon atoms inclusive, hydroxy, amino, alkylthio of from 1 to 4 carbon atoms inclusive, halogen, trifluoromethyl, alkanoamido of 1 to 6 carbon atoms inclusive, and alkanesulfonamido of 1 to 6 carbon atoms inclusive, and a non-toxic pharmaceutically acceptable acid addition salt thereof.

2. The process of claim 1 comprising the administration of 8-[4-[4-(2-pyrimidinyl)-1-piperazinyl]butyl]-8-azaspiro[4.5]-decane-7,9-dione.

3. The process of claim 1 comprising the administration of 8-[4-[4-(2-pyrimidinyl)-1-piperazinyl]butyl]-8-azaspiro[4.5]-decane-7,9-dione hydrochloride.

4. The process of claim 1 comprising the administration of 8-[4-[4-(2-pyridyl)-1-piperazinyl]butyl]-8-azaspiro[4.5]decane-7,9-dione.

5. The process of claim 1 comprising the administration of 8-[4-[4-(2-pyridyl)-1-piperazinyl]butyl]-8-azaspiro[4.5]decane-7,9-dione hydrochloride.

6. The process of claim 1 comprising the administration of 8-[2-[4-(2-pyridyl)-1-piperazinyl]ethyl]-8-azaspiro[4.5]decane-7,9-dione.

7. The process of claim 1 comprising the administration of 8-[2-[4-(2-pyridyl)-1-piperazinyl]ethyl]-8-azaspiro[4.5]decane-7,9-dione hydrochloride.

8. The process of claim 1 comprising the administration of 8-[2-[4-(2-pyrimidinyl-1-piperazinyl]ethyl]-8-azaspiro[4.5]-decane-7,9-dione.

9. The process of claim 1 comprising the administration of 8-[2-[4-(2-pyrimidinyl)-1-piperazinyl]ethyl]-8-azaspiro[4.5]-decane-7,9-dione hydrochloride.

10. The process of claim 1 comprising the administration of 8-[3-[4-(2-pyrimidinyl)-1-piperazinyl]propyl]-8-azaspiro[4.5]-decane-7,9-dione.

11. The process of claim 1 comprising the administration of 8-[3-[4-(2-pyrimidinyl)-1-piperazinyl]propyl]-8-azaspiro[4.5]-decane-7,9-dione hydrochloride.

12. The process of claim 1 comprising the administration of 8-[5-[4-(2-pyrimidinyl)-1-piperazinyl]pentyl]-8-azaspiro[4.5]-decane-7,9-dione.

13. The process of claim 1 comprising the administration of 8-[5-[4-(2-pyrimidinyl)-1-piperazinyl]pentyl]-8-azaspiro[4.5]-decane-7,9-dione hydrochloride.

14. The process of clam 1 comprising the administration of 8-[3-[4-(6-methoxy-2-pyridyl)-2-piperazinyl]propyl]-8-azaspiro-[4.5]decane-7,9-dione.

15. The process of clam 1 comprising the administration of 8-[3-[4-(6-methoxy-2-pyridyl)-1-piperazinyl]propyl]-8-azaspiro-[4.5]decane-7,9-dione hydrochloride.

16. The process of claim 1 comprising the administration of 3-[4-[4-(2-pyrimidinyl)-1-piperazinyl]butyl]-3-azaspiro[5.5]-undecane-2,4-dione.

17. The process of claim 1 comprising the administration of 3-[4-[4-(2-pyrimidinyl)-1-piperazinyl]butyl]-3-azaspiro[5.5]-undecane-2,4-dione hydrochloride.

18. The process of claim 1 comprising the administration of 8-[4-[4-(4,6-dimethyl-2-pyrimidinyl)-1-piperazinyl]butyl]-8-azaspiro[4.5]decane-7,9-dione.

19. The process of claim 1 comprising the administration of 8-[4-[4-(4,6-dimethyl-2-pyrimidinyl)-1-piperazinyl]butyl]-8-azaspiro[4.5]decane-7,9-dione hydrochloride.

20. A pharmaceutical composition in dosage unit form suitable for systemic administration to a mammalian host comprising a pharmaceutical carrier and sufficient compound to provide an effective daily dose of from 0.01 to 40 mg./kg. of body weight of said host, said compound being selected from the group consisting of compounds of the formula:

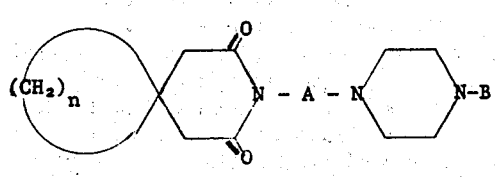

wherein
n is the integer 4 or 5;

A is a divalent straight or branched alkylene chain of 2 to 6 carbon atoms inclusive and connects the nitrogen atoms as shown through at least 2 carbon atoms;

B is a heteroarcyclic represented by the symbol wherein

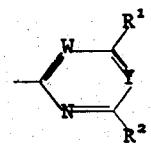

W and Y are independently selected from the group consisting of CH and nitrogen, $R^1$ and $R^2$ are independently selected from the group consisting of hydrogen, lower alkyl from 1 to 4 carbon atoms inclusive, lower alkoxy of from 1 to 4 carbon atoms inclusive, hydroxy, amino, alkylthio of 1 to 4 carbon atoms inclusive, halogen, trifluoromethyl, alkanoamido of 1 to 6 carbon atoms inclusive, and alkanesulfonamido of 1 to 6 carbon atoms inclusive, and a non-toxic pharmaceutically acceptable acid addition salt thereof.

21. The composition of claim 20 containing 8-[4-[4-(2-pyrimidinyl)-1-piperazinyl]butyl]-8-azaspiro[4.5]-decane-7,9-dione.

22. The composition of claim 20 containing 8-[4-[4-(2-pyrimidinyl)-1-piperazinyl]butyl]-8-azaspiro[4.5]-decane-7,9-dione hydrochloride.

23. The composition of claim 20 containing 8-[4-[4-(2-pyridyl)-1-piperazinyl)]butyl]-8-azaspiro[4.5]decane-7,9-dione.

24. The composition of claim 20 containing 8-[4-[4-(2-pyridyl)-1-piperazinyl)]butyl]-8-azaspiro[4.5]decane-7,9-dione hydrochloride.

25. The composition of claim 20 containing 8-[4-[4-(2-pyridyl)-1-piperazinyl]ethyl]-8-azaspiro[4.5]decane-7,9-dione.

26. The composition of claim 20 containing 8-[2-[4-(2-pyridyl)-1-piperazinyl]ethyl]-8-azaspiro[4.5]decane-7,9-dione hydrochloride.

27. The composition of claim 20 containing 8-[2-[4-(2-pyrimidinyl)-1-piperazinyl]ethyl]-8-azaspiro[4.5]-decane-7,9-dione.

28. The composition of claim 20 containing 8-[2-[4-(2-pyrimidinyl)-1-piperazinyl]ethyl]-8-azaspiro[4.5]-decane-7,9-dione hydrochloride.

29. The composition of claim 20 containing 8-[3-[4-(2-pyrimidinyl)-1-piperazinyl]propyl]-8-azaspiro[4.5]-decane-7,9-dione.

30. The compositon of claim 20 containing 8-[3-[4-(2-pyrimidinyl)-1-piperazinyl]propyl]-8-azaspiro[4.5]-decane-7,9-dione hydrochloride.

31. The composition of claim 20 containing 8-[5-[4-(2-pyrimidinyl)-1-piperazinyl]pentyl]-8-azaspiro[4.5]-decane-7,9-dione.

32. The composition of claim 20 containing 8-[5-[4-(2-pyrimidinyl)-1-piperazinyl]pentyl]-8-azaspiro[4.5]-decane-7,9-dione hydrochloride.

33. The composition of claim 20 containing 8-[3-[4-(6-methoxy-2-pyridyl)-1-piperazinyl]propyl]-8-azaspiro[4.5]decane-7.9-dione.

34. The composition of claim 20 containing 8-[3-[4-(6-methoxy-2-pyridyl)-1-piperazinyl]propyl]-8-azaspiro[4.5]decane-7,9-dione hydrochloride.

35. The composition of claim 20 containing 3-[4-[4-(2-pyrimidinyl)-1-piperazinyl]butyl]-3-azaspiro[5.5]undecane-2,4-dione.

36. The composition of claim 20 containing 3-[4-[4-(2-pyrimidinyl)-1-piperazinyl]butyl]-3-azaspiro[5.5]undecane-2,4-dione hydrochloride.

37. The composition of claim 20 containing 8-[4-[4-(4,6-dimethyl-2-pyrimidinyl)-1-piperazinyl]butyl]-8-azaspiro[4.5]-decane-7,9-dione.

38. The composition of claim 20 containing 8-[4-[4-(4,6-dimethyl-2-pyrimidinyl)-1-piperazinyl]butyl]-8-azaspiro[4.5]-decane-7,9-done hydrochloride.

\* \* \* \* \*